(12) United States Patent
Lim et al.

(10) Patent No.: US 11,039,800 B2
(45) Date of Patent: Jun. 22, 2021

(54) UPRIGHT POSTURE ASSISTING DEVICE FOR X-RAY INSPECTION OF INFANTS

(71) Applicant: CHONBUK NATIONAL UNIVERSITY HOSPITAL, Jeonju-si (KR)

(72) Inventors: Ho Tae Lim, Jeonju-si (KR); Myoung Hwan Ko, Jeonju-si (KR); Kap Soo Han, Suwon-si (KR)

(73) Assignee: CHONBUK NATIONAL UNIVERSITY HOSPITAL, Jeonju-si (KR)

( * ) Notice: Subject to any disclaimer, the term of this patent is extended or adjusted under 35 U.S.C. 154(b) by 0 days.

(21) Appl. No.: 16/613,424

(22) PCT Filed: May 15, 2018

(86) PCT No.: PCT/KR2018/005556
§ 371 (c)(1),
(2) Date: Nov. 14, 2019

(87) PCT Pub. No.: WO2018/212559
PCT Pub. Date: Nov. 22, 2018

(65) Prior Publication Data
US 2020/0100735 A1 Apr. 2, 2020

(30) Foreign Application Priority Data
May 15, 2017 (KR) .................. 10-2017-0059685

(51) Int. Cl.
*A61B 6/04* (2006.01)
(52) U.S. Cl.
CPC ................. *A61B 6/0421* (2013.01)

(58) Field of Classification Search
CPC ................. A61B 6/0421; A61B 6/04
See application file for complete search history.

(56) References Cited

U.S. PATENT DOCUMENTS

| 2,757,997 | A | * | 8/1956 | Lee | ........................ | A61B 6/04 |
| | | | | | | 5/601 |
| 2,926,256 | A | * | 2/1960 | Rankin | ................ | A61B 6/0421 |
| | | | | | | 378/174 |
| 4,464,780 | A | * | 8/1984 | Ruiz | .................... | A61B 6/0421 |
| | | | | | | 378/178 |

FOREIGN PATENT DOCUMENTS

| CN | 2650708 Y | 10/2004 |
| JP | 3770069 B2 | 4/2006 |
| KR | 20040095603 A | 11/2004 |
| KR | 101163125 B1 | 7/2012 |
| KR | 101727484 B1 | 5/2017 |

* cited by examiner

*Primary Examiner* — Chih-Cheng Kao
(74) *Attorney, Agent, or Firm* — Dragon Sun Law Firm, PC; Jinggao Li, Esq.

(57) ABSTRACT

An upright posture assisting device for an X-ray inspection of infants, and more particularly to an upright posture assisting device for an X-ray inspection of infants, by which an infant can be X-ray photographed while being safely fixed. The upright posture assisting device for an X-ray inspection of infants includes: a body disposed on the front side of an X-ray detector and having an empty space in the interior thereof; an insertion hole formed on the upper surface of the body such that the legs of an infant are inserted into the insertion hole; and handgrip parts mounted on opposite sides of the upper surface of the body.

8 Claims, 8 Drawing Sheets

UPRIGHT POSTURE ASSISTING DEVICE FOR X-RAY INSPECTION OF INFANTS

CROSS-REFERENCES TO THE RELATED APPLICATIONS

This application is the national phase entry of International Application No. PCT/KR2018/005556, filed on May 15, 2018, which is based upon and claims priority to Korean Patent Application No. 10-2017-0059685, filed on May 15, 2017, the entire contents of which are incorporated herein by reference.

TECHNICAL FIELD

The present invention relates to an upright posture assisting device for an X-ray inspection of infants, and more particularly to an upright posture assisting device for an X-ray inspection of infants, by which an infant can be X-ray photographed while being safely fixed.

BACKGROUND

X-ray photographing is one of medical acts that are essential in the modern society, by which the state of a patient can be recognized by irradiating a highly radioactive ray.

However, because an X ray is accompanied with a danger due to the high radioactivity, the user and the patient have to finish photographing of one time if possible.

However, when an infant who does not recognize the danger is photographed, the frequency of repeated photographing is high due to the movement or an unstable posture of the infant.

Accordingly, although a guardian and an assistant hold the infant for photographing to prevent repeated photographing of the infant who are rather distracted, the guardian and the assistant have a danger of exposure to a radioactive ray during x-ray photographing.

Further, a hand and the like of the guardian who holds the body of the infant may be photographed, which may act as an error or disorder factor in the inspection.

An assisting device for fixing an infant has been developed to solve the problem, but infants are held unstably, causing repeated photographing, and the infants may fall down from the assisting device.

SUMMARY

The present invention has been made in an effort to solve the problems, and provides an upright posture assisting device for an X-ray inspection of infants, by which an infant can be safely fixed while the infant is not held so that X-ray photographing can be made precisely and easily, and a guardian or the like can be prevented from being exposed to an radioactive ray.

An upright posture assisting device for an X-ray inspection of infants according to an aspect of the present invention may include: a body disposed on the front side of an X-ray detector and having an empty space in the interior thereof; an insertion hole formed on the upper surface of the body such that the legs of an infant are inserted into the insertion hole; and handgrip parts mounted on opposite sides of the upper surface of the body.

A pair of side fixing members that contacts a side surface of the infant to fix the infant may be formed on opposite sides of the upper surface of the body, and the handgrip parts are coupled to an upper portion of the side fixing members.

The side fixing members may be mounted on the body to be movable leftwards and rightwards.

The side fixing members may include: a pair of support plates disposed on opposite sides of the insertion hole and contacting the side surface of the infant; and guide bosses protruding horizontally from the support plates, and rail grooves, on which the guide bosses are seated to be moved, may be formed in the body.

The upright posture assisting device may further include: stop members configured to fix the guide boss that are moved along the rail grooves.

The body may have first through-holes that pass through the rail grooves, second through-holes may be formed in the guide bosses, the number of the first through-holes or the second through-holes may be plural, and the stop members may have a pin shape and are inserted into the first through-holes and the second through-holes to fix the guide bosses.

An impact absorber, through which an X ray passes, may be coupled to inner surfaces of the support plates, which contact the side surface of the infant.

The upright posture assisting device may further include: a front stop/protection member connecting the pair of spaced side fixing members in the forward direction of the body, and the front stop/protection member may be formed of a material, through which the X ray passes.

A footplate that supports the feet of the infant, whose lower body is disposed in the interior of the body, may be mounted on a lower portion of the body, and the footplate may be mounted to be movable upwards and downwards with respect to the body.

The upright posture assisting device may further include: a seating part, on which a lower portion of the X-ray detector is seated, is formed on the rear side of the body, and a stopper step, which is stepped by the rear surface of the X-ray detector, protrudes from the rear side of the seating part.

The upright posture assisting device for an X-ray inspection of infants of the present invention, which has been described above, has the following effects.

According to the assisting device of the present invention, the infant may be fixed safely by the side fixing members and the like while the infant is not held by a guardian when the infant is X-ray photographed so that the X-ray photographing may be made precisely and easily.

Further, the guardian may be prevented from being exposed to a radioactive ray because he or she does not hold the infant, and the precision of the inspection may be further increased as only the body of the infant is photographed through an X ray.

BRIEF DESCRIPTION OF THE DRAWINGS

The above and other objects, features, and advantages of the present invention will be more apparent from the following detailed description taken in conjunction with the accompanying drawings, in which.

DETAILED DESCRIPTION OF THE EMBODIMENTS

An upright posture assisting device for an X-ray inspection of infants according to the present invention, as illustrated in FIGS. 1 to 7, includes a body 10, side fixing members 20, and handgrip parts 30.

The body 10 is disposed on the front side of the X-ray detector 50, and has an empty space in the interior thereof.

The detector 50 includes a generally used DR detector.

Although the body 10 has a hexagonal shape in the drawings of the embodiment, it may have a shape that is different from a hexagonal shape.

Insertion holes 11, through which the legs of the infant are inserted, are formed on the upper surface of the body 10.

One insertion hole 11 may be provided such that all the legs are inserted into the insertion hole 11, or two insertion holes may be formed as in the drawings of the embodiment such that the legs are inserted into the insertion holes 11, respectively.

When two insertion holes 11 are formed, it is preferable that an impact absorber, such as sponge, is disposed between the two insertion holes 11 such that the two legs of the infant are not uncomfortable.

Further, a seating part 14, on which a lower portion of the X-ray detector 50 is seated, is formed on the rear side of the body 10, and a stopper step 15, by which the rear surface of the X-ray detector 50 is stopped, protrudes from the rear side of the seating part 14.

Through the seating part 14 and the stopper step 15, the X-ray detector 50 and the body 10 are coupled to each other by the stopper step 15 when a lower portion of the X-ray detector 50 is seated on the seating part 14 so that the body 10 may be prevented from being separated or spaced apart from the X-ray detector 50.

The side fixing members 20 are formed on the opposite sides of the upper surface of the body 10 to contact the side surface of the infant, such as a pelvis or a side of the infant so that the infant may maintain the fixed state without being shaken leftwards or rightwards.

The side fixing members 20 are mounted on the body 10 to be movable leftwards and rightwards so that the sizes of the side fixing member 20 vary according to the size of the body of the infant.

The side fixing members 20 include support plates 21 and guide bosses 22.

The support plates 21 are two plates which are disposed on opposite sides of the insertion holes 11 and contact the side surface of the infant.

Impact absorbers (not illustrated), through which an X ray passes, is coupled to inner surfaces of the support plates 21, that is, the surfaces of the support plates 21 which contact the side surface of the infant, and the support plates 21 strongly press the side surface of the infant to prevent an accident.

It is preferable that the impact absorber is formed of sponge, through which the X ray passes.

The guide bosses 22 protrude horizontally from the support plates 21.

Further, rail grooves 12, on which the guide bosses 22 are seated to be moved, are formed in the body 10 to be horizontally recessed.

Accordingly, when the side fixing members 20 are moved leftwards and rightwards, the guide bosses 22 may be moved along the rail grooves 12 so that the side fixing members 20 are moved stably leftwards and rightwards with respect to the body 10.

Then, the present invention may further include stop members 25 for fixing the guide bosses 22 that are moved along the rail grooves 12.

The stop members 25 have various conventional known structures to prevent the guide bosses 22 from moving.

In order to prevent the guide bosses 22 from moving, in the embodiment, first through holes 13, which pass through the rail grooves 12, are formed in the body 10 and second through-holes 23 are formed in the guide bosses 22.

Then, one of the numbers of the first through-holes 13 or the second through-holes 23 is plural, and the stop members 25 have a pin shape so that the stop members 25 are inserted into the first through-holes 13 and the second through-holes 23 such that the guide bosses 22 are fixed.

The side fixing members 20 may not be provided, but when they are provided, the infant, whose lower body is inserted into the insertion hole 11 of the body 10, may be prevented from being shaken leftwards and rightwards.

The handgrip parts 30 are coupled to upper portions 20 of the side fixing members 20 such that the infant may grip the handgrip parts 30.

When the side fixing members 20 are not provided, the handgrip parts 30 may be mounted on opposite sides of the upper surface of the body 10.

Further, the present invention may further include a front stop/protection member 40 that connects the pair of spaced side fixing members 20 in the forward direction of the body 10.

The front stop/protection member 40 includes a wire or a bar, and may prevent the infant from being bent forwards and the length of the front stop/protection member 40 may be adjusted.

Then, the front stop/protection member 40 is formed of various materials, through which the X ray may passes.

Further, a footplate 19 that supports the feet of the infant, whose lower body is disposed in the interior of the body 10, may be mounted on a lower portion of the body 10.

Then, the footplate 19 is mounted on the body 10 to be movable upwards and downwards.

To achieve this, in the embodiment, a slide hole 18 is formed on a side surface of the body 10, and a support rod 19a that is inserted into the slide hole 18 to be stopped after moving upwards and downwards is mounted on the foot plate 19.

A stop hole 18a is formed in the slide hole 18 such that the footplate 19 maintains a stop state when the support rod 19a is inserted into the stop hole 18a.

Because the footplate 19 is mounted to be movable upwards and downwards, the infant may stands stably on the footplate 19 while moving the footplate 19 upwards and downwards according to the height of the infant.

Hereinafter, a usage of the present invention including the above configuration will be described.

First, the legs of the infant are inserted into the insertion holes 11 formed at an upper portion of the body 10.

Figure 1:
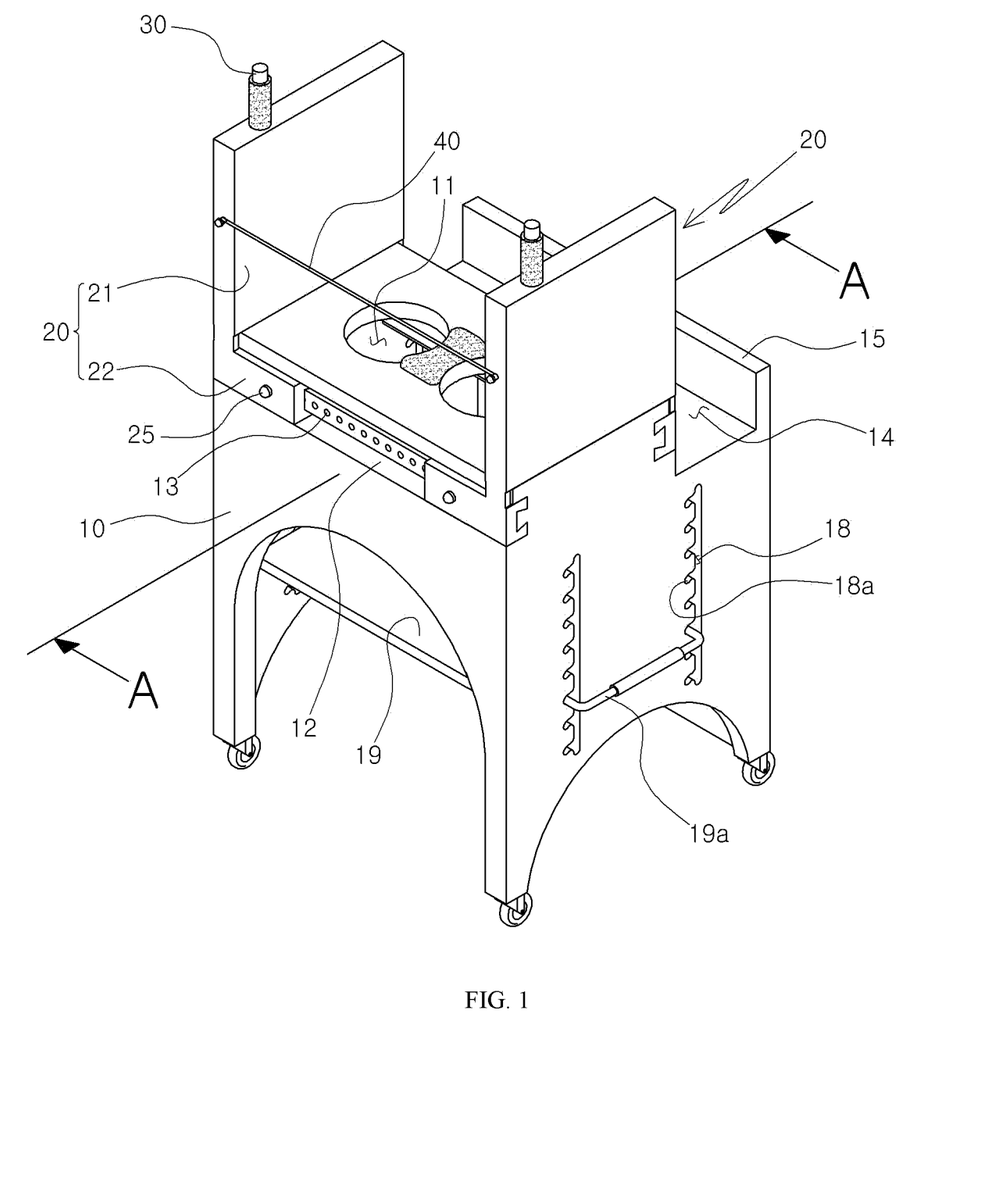
FIG. 1 shows a perspective view of an upright posture assisting device for an X-ray inspection of infants according to an embodiment of the present invention.
Figure 2:
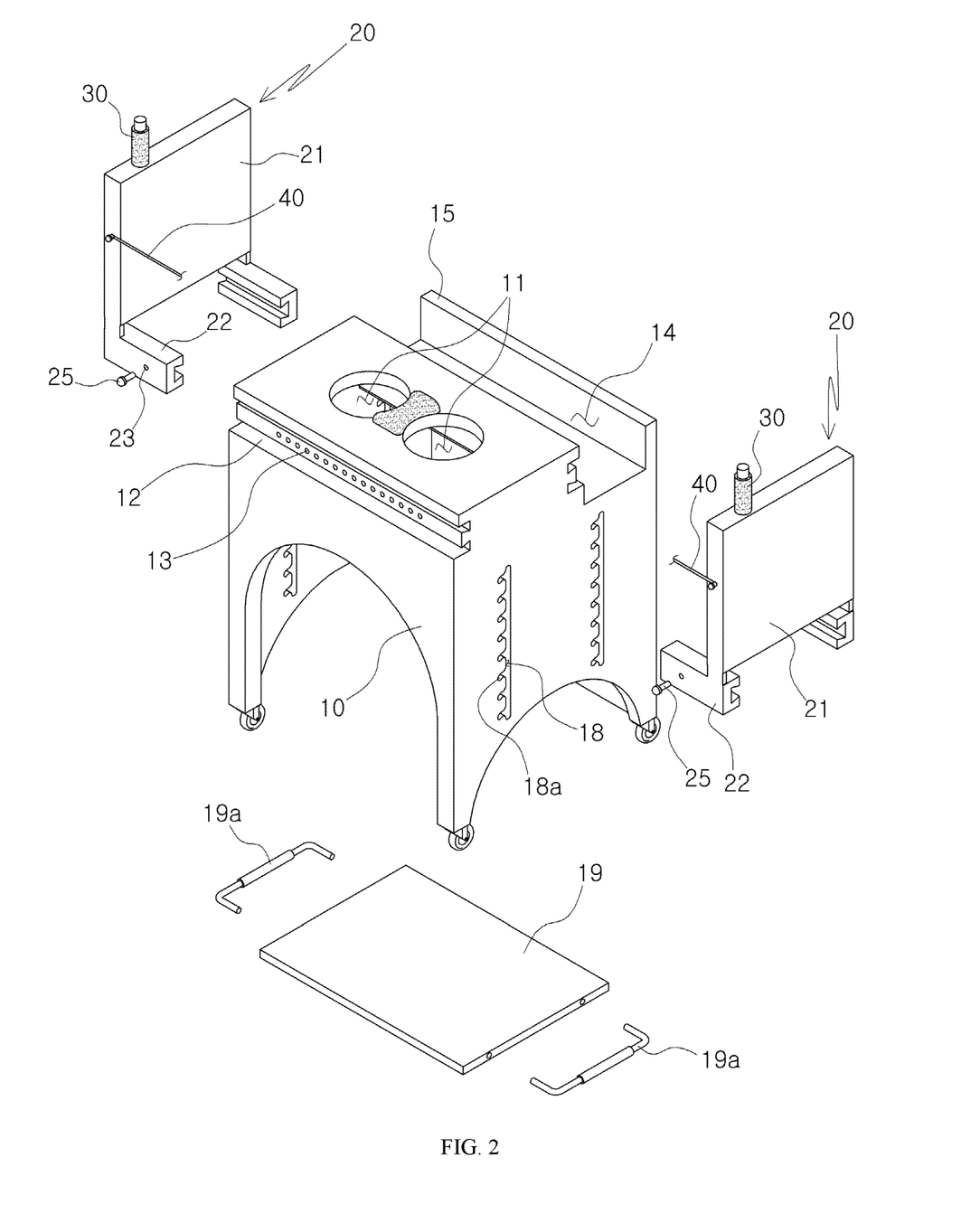
FIG. 2 shows an exploded perspective view of the upright posture assisting device for an X-ray inspection of infants according to the embodiment of the present invention.
Figure 3:
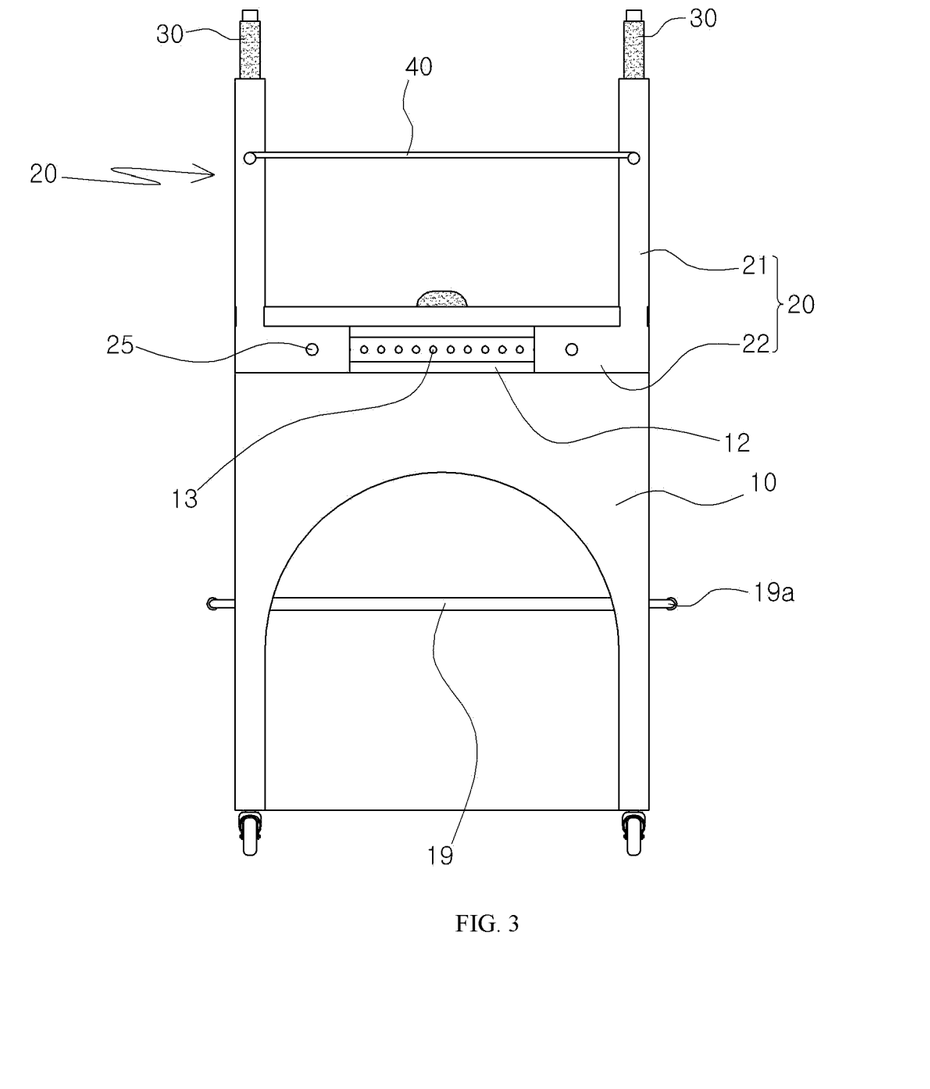
FIG. 3 shows a front view of the upright posture assisting device for an X-ray inspection of infants according to the embodiment of the present invention.
Figure 4:
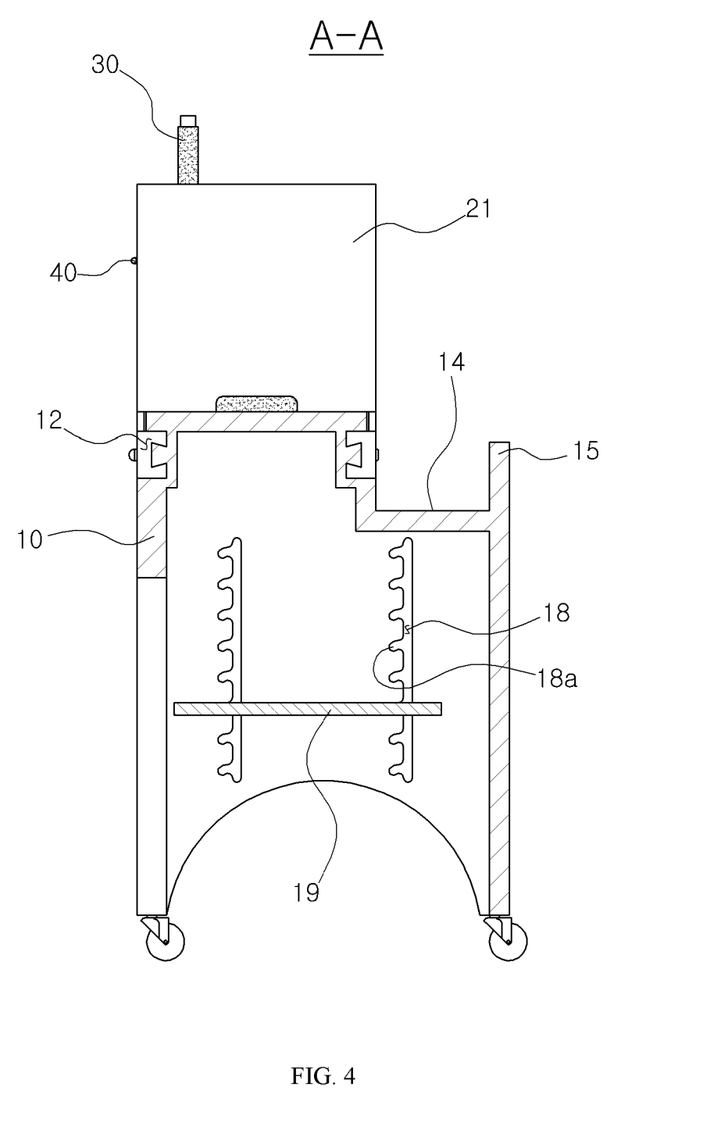
FIG. 4 shows a sectional view taken along line A-A of FIG. 1.
Figure 5A:
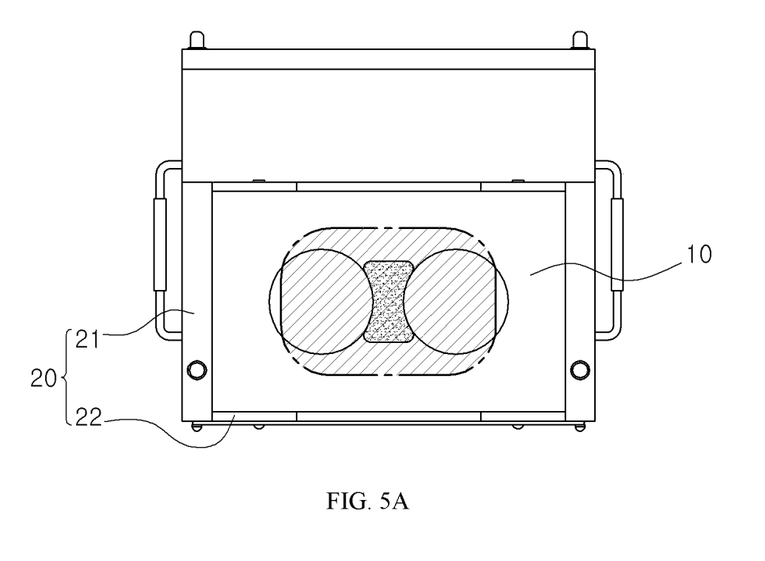
FIGS. 5A and 5B are views illustrating an operational process of a side fixing member of the upright posture assisting device for an X-ray inspection of infants according to the embodiment of the present invention.
Figure 5B:
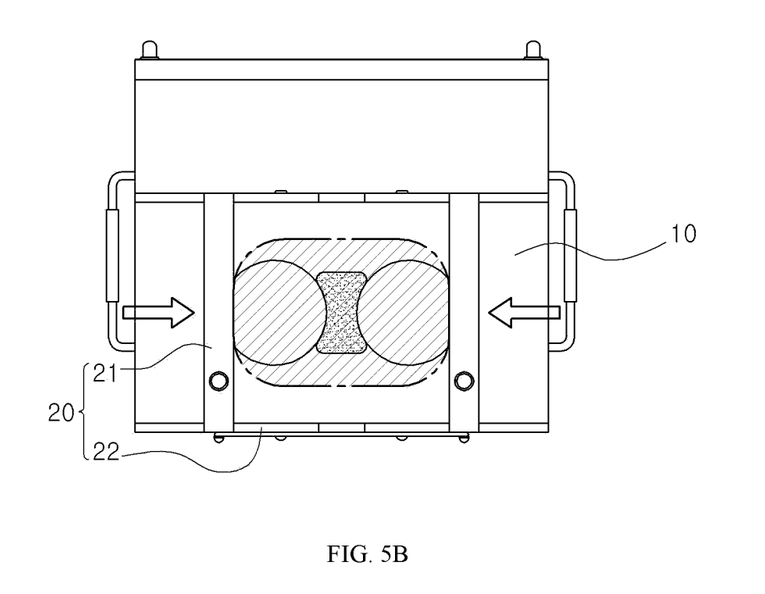

Thereafter, as illustrated in FIGS. 5A and 5B, the side surface of the infant is fixed by using the side fixing members 20.

In more detail, if the assisting device is moved while the infant grips the support plates 21, the guide bosses 22 are moved along the rail grooves 12.

If the support plates 21 contact the side surface of the infant, the stop members 25 pass through the first through-holes 13 and the second through-holes 23 to stop movement of the side fixing members 20.

The infant may maintain a fixed state without being shaken leftwards and rightwards due to the side fixing members 20.

Thereafter, the front stop/protection member 40 is installed to prevent the infant disposed at an upper portion of the body 10 from moving forwards.

Figure 7:
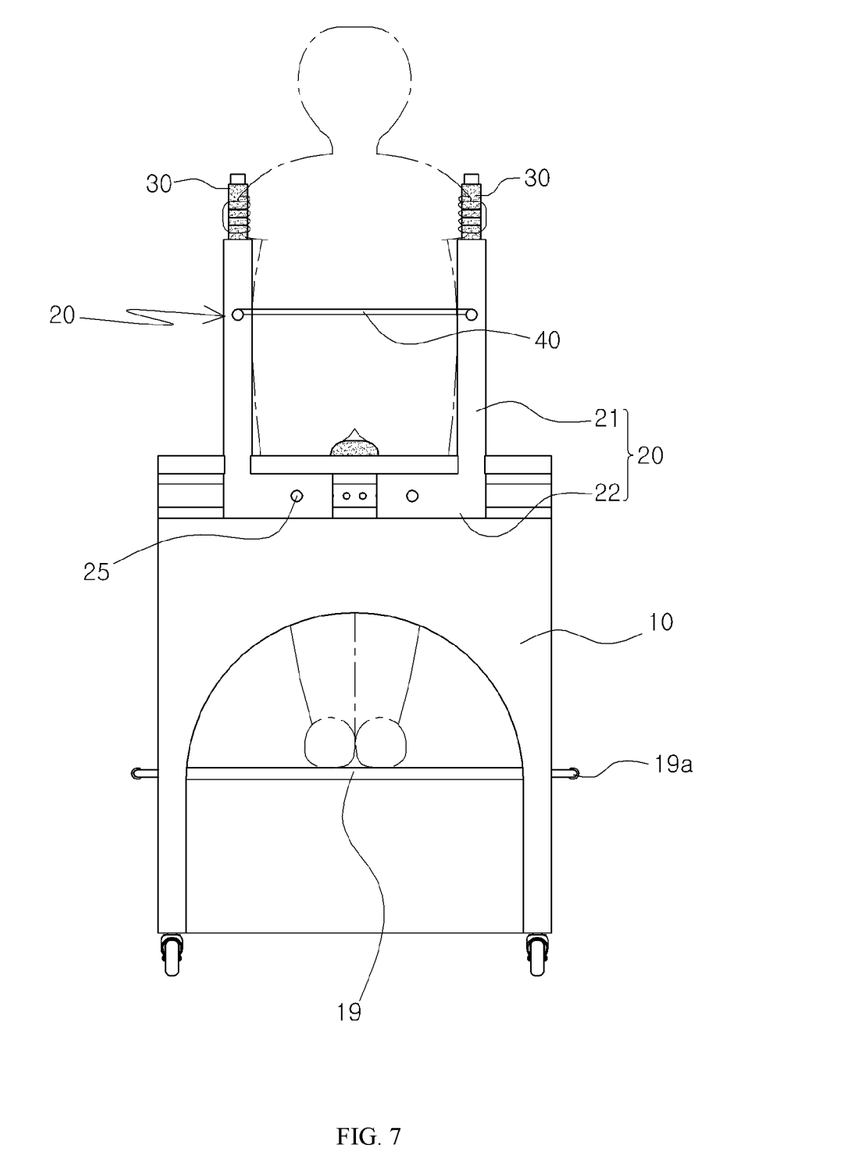
FIG. 7 shows a front view of a state in which an infant is on the upright posture assisting device for an X-ray inspection of infants according to the embodiment of the present invention.

If the process is ended, the state becomes the state as illustrated in FIG. 7.

Figure 6A:
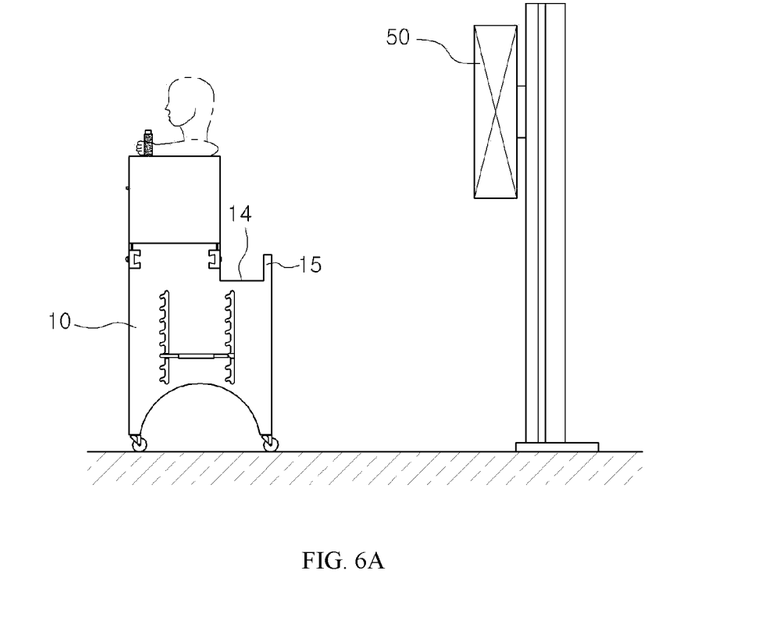
FIGS. 6A, 6B and 6C are side views illustrating a of coupling the upright posture assisting device for an X-ray inspection of infants to an X-ray detector according to the embodiment of the present invention.

If the riding and fixing of the infant is ended, as illustrated in FIG. 6A, the X-ray detector 50 is lifted.

Figure 6B:
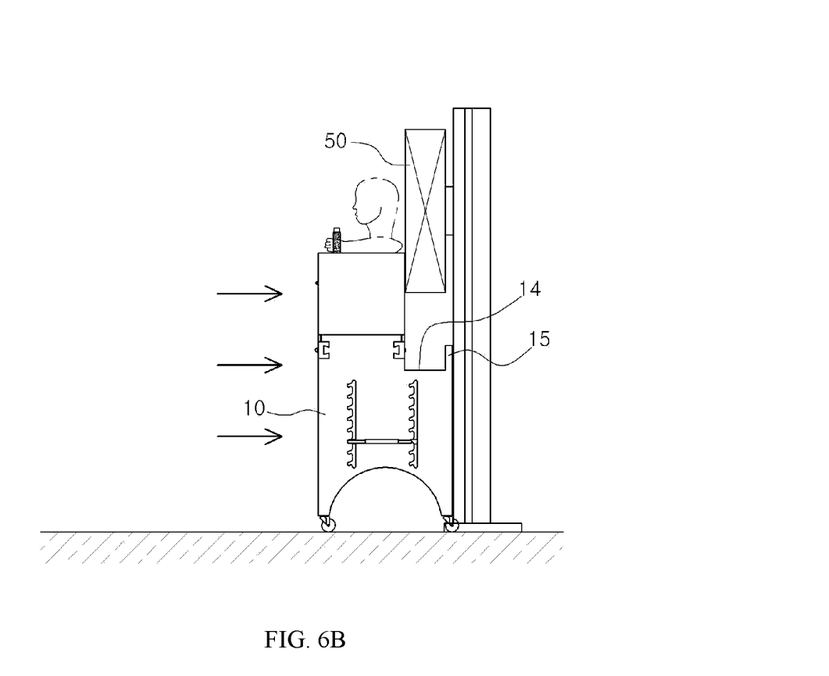

Thereafter, as illustrated in FIG. 6B, the assisting device of the present invention is moved to a site of the X-ray detector 50.

Figure 6C:
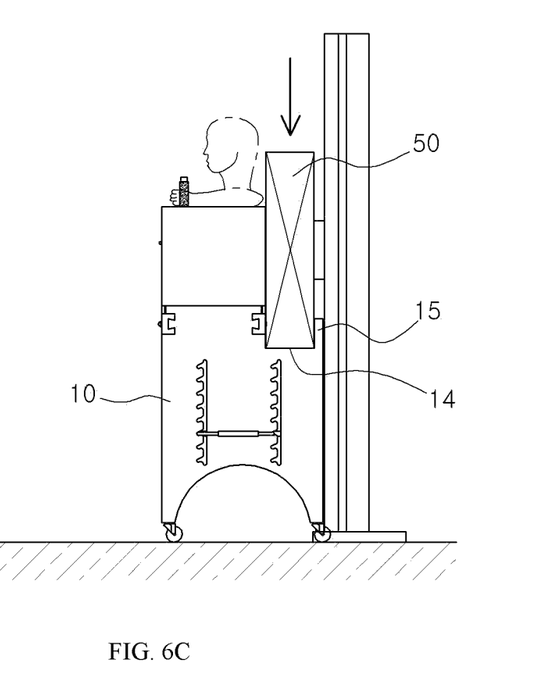

Further, as illustrated in FIG. 6C, the X-ray detector 50 is lowered.

Then, a lower portion of the X-ray detector 50 is seated on the seating part 14 formed on the rear side of the body 10.

Then, the stopper step 15 is formed at a lower portion of the seating part 14, and the stopper step 15 is stepped by the rear surface of the X-ray detector 50.

Accordingly, the wheels are provided at a lower portion of the body 10, but because the X-ray detector 50 is coupled to the body 10 by the seating part 14 and the stopper step 15, an X-ray inspection may be performed in the state in which the body 10 is stopped without moving accidently.

According to the assisting device of the present invention, the infant may be fixed safely while the infant is not held by a guardian when the infant is X-ray photographed so that the X-ray photographing may be made precisely and easily.

Further, the guardian may be prevented from being exposed to a radioactive ray because he or she does not hold the infant, and the precision of the inspection may be further increased as only the body of the infant is photographed through an X ray.

The upright posture assisting device for an X-ray inspection of infants of the present invention is not limited to the above-described embodiment, and may be variously modified within a range that is allowed by the technical sprit of the present invention.

INDUSTRIAL APPLICABILITY

The present invention may be applied to an assisting device that maintains a standing state of an infant during an X-ray inspection, and thus can be industrially applicable.

What is claimed is:

1. An upright posture assisting device for an X-ray inspection of infants, comprising:
    a body configured to be disposed on a front side of an X-ray detector and having an empty space in an interior thereof;
    an insertion hole formed on an upper surface of the body, wherein, the insertion hole is configured for a plurality of legs of an infant to be inserted into the insertion hole;
    a plurality of handgrip parts mounted on a plurality of opposite sides of an upper surface of the body; and
    a pair of side fixing members configured to contact a side surface of the infant to fix the infant, wherein, the pair of side fixing members is formed on the plurality of opposite sides of the upper surface of the body, and the plurality of handgrip parts are coupled to an upper portion of the pair of side fixing members,
    wherein the pair of side fixing members is mounted on the body to be movable leftwards and rightwards.

2. The upright posture assisting device of claim 1, wherein, each side fixing member comprises: a pair of support plates disposed on opposite sides of the insertion hole and are configured for contacting the side surface of the infant; and a plurality of guide bosses protruding horizontally from the pair of support plates, and
    wherein a plurality of rail grooves is formed in the body, the plurality of guide bosses is seated on the plurality of rail grooves and are configured to move along the plurality of rail grooves.

3. The upright posture assisting device of claim 2, further comprising:
    a plurality of stop members configured to fix the plurality of guide bosses.

4. The upright posture assisting device of claim 3, wherein the body has a plurality of first through-holes passing through the plurality of rail grooves, a plurality of second through-holes is formed in the plurality of guide bosses, and the plurality of stop members have a pin shape and are inserted into the plurality of first through-holes and the plurality of second through-holes to fix the plurality of guide bosses.

5. The upright posture assisting device of claim 2, further comprising an impact absorber coupled to a plurality of inner surfaces of the plurality of support plates.

6. The upright posture assisting device of claim 1, further comprising:
    a front stop/protection member connecting the pair of side fixing members in a forward direction of the body.

7. The upright posture assisting device of claim 1, wherein a footplate configured to support feet of the infant, is mounted on a lower portion of the body, and the footplate is configured to be movable upwards and downwards with respect to the body.

8. The upright posture assisting device of claim 1, further comprising:
    a seating part formed on a rear side of the body, wherein a lower portion of the X-ray detector is seated on the seating part, and a stopper step, and the stopper step is stepped by the rear surface of the X-ray detector and protrudes from a rear side of the seating part.

* * * * *